United States Patent [19]
Ritter

[11] Patent Number: 6,166,159
[45] Date of Patent: Dec. 26, 2000

[54] HIGH-STRENGTH DEGRADABLE MATERIALS AND MOLDED ARTICLES FOR IMPLANTATION INTO HUMAN AND ANIMAL ORGANISMS

[75] Inventor: Wolfgang Ritter, Haan, Germany

[73] Assignee: Merck Patent GmbH, Darmstadt, Germany

[21] Appl. No.: 08/066,087

[22] PCT Filed: Nov. 18, 1991

[86] PCT No.: PCT/EP91/02169

§ 371 Date: May 26, 1993

§ 102(e) Date: May 26, 1993

[87] PCT Pub. No.: WO92/09313

PCT Pub. Date: Jun. 11, 1992

[30] Foreign Application Priority Data

Nov. 26, 1990 [DE] Germany ............................. 40 37 516

[51] Int. Cl.[7] ............................... C08F 20/28; A61F 2/02
[52] U.S. Cl. ..................... 526/323.1; 526/320; 606/77; 623/11
[58] Field of Search ................................. 526/323.1, 320; 606/77; 623/11

[56] References Cited

U.S. PATENT DOCUMENTS 4,626,310  12/1986  Ritter ..................................... 156/307.3
4,731,425   3/1988  Ritter ......................................... 526/196

FOREIGN PATENT DOCUMENTS 3825211  2/1990  Germany .
3826915  2/1990  Germany .
3843854  6/1990  Germany .
3843930  6/1990  Germany .
3843938  6/1990  Germany .
3843843  7/1990  Germany .
3939161  5/1991  Germany .
3939162  5/1991  Germany .

OTHER PUBLICATIONS

Encyclopedia of Polymer Science and Engineering (2nd Edition) vol. 11, 187–207.
Progress in Polymer Sciience, vol. 8, Pergamon Press, Oxford—New York, 1982, pp. 61–131.

*Primary Examiner*—Bernard Lipman
*Assistant Examiner*—N. Sarofim
*Attorney, Agent, or Firm*—Wayne C. Jaeschke; John Daniel Wood; Real J. Grandmaison

[57] ABSTRACT

Described are high-strength materials which are degradable and resorbable in the human and animal organisms and shaped articles manufactured therefrom, such as implants, based on cured (meth)acrylic acid esters of polyfunctionally hydroxyl-terminated oligomers of lower hydroxycarboxylic acids {polyfunctional (meth)acrylic acid esters}. The invention is characterized in that said materials and/or shaped articles have been three-dimensionally cross-linked by radiation-curing and/or any other, however boron-free, free radical-initiated polymerization of the polyfunctional (meth) acrylic acid esters and exhibit a tensile strength under standard conditions of at least 10 $N/mm^2$.

57 Claims, No Drawings

HIGH-STRENGTH DEGRADABLE MATERIALS AND MOLDED ARTICLES FOR IMPLANTATION INTO HUMAN AND ANIMAL ORGANISMS

BACKGROUND OF THE INVENTION

1. Field of the Invention

The invention relates to novel plastics-based high-strength materials and molded articles manufactured therefrom, which are degradable and resorbable in the human and animal organisms.

2. Discussion of Related Art

In the techniques of clinical surgery, substituting resorbable organic polymers for metal implants is desirable, because thereby a second surgery for removing the implants is rendered unnecessary. Today, resorbable suture materials and resorbable pins for the fixation of bone fragments are known in practical use. These materials used hitherto have been made of poly(lactic acid), poly(glycolic acid), poly(dioxanone) or of copolymers thereof.

The technical utilization of such materials in the form of resorbable plates, screws, nails and the like has failed to come so far. This is due to the following shortcomings, among others, of the materials known till today: The strength of the polymer is too low so that, for example, upon the use of said materials as bolts the heads crack off. There is a high dependency on the predetermined molar weight of the ultimate strength. Processing said materials is extremely expensive.

DE-A1 32 29 635 describes surgical binder systems for adhesion-bonding endogenous hard tissue optionally to plastics and/or metal. Here provided is a resorbable (meth)acrylate component which is liquid to solid at room temperature and consists of (meth)acrylic acid esters with (meth)acrylate moieties on oligoester chains of hydroxycarboxylic acids, said oligoesters having been formed of lower monohydroxymonocarboxylic acids. Here, organoboron compounds have been compulsorily prescribed as the polymerization initiator, which compounds are distinguished by a particularly high activity with respect to polymerization initiation. Said printed publication reporting results of Applicants' own studies was based on the recognition, that the combination of organoboron compounds as the initiator system with, more particularly, the polyfunctional (meth)acrylic acid esters can be especially appropriate for the necessary curing process to form high-strength joint bonds in the area of surgical adhesives.

In this older protective right there has also been referred to the demand for using resorbable supporting materials in surgical techniques, so that a second surgery as otherwise required would be rendered superfluous. Accordingly, in addition to the use of the reactive two-component system, said printed publication describes the use thereof for the in situ manufacture of resorbable molded articles in adhesion-bonding endogenous hard tissue, optionally together with plastics and/or metal. One indispensable component of the molded article formed thereby and, thus, an ingredient of the molded article to be implanted into the living organism is constituted by the organoboron compounds employed as initiators. To this day, materials of this kind have not gained general acceptance in practical use.

DESCRIPTION OF THE INVENTION

The teaching of the present invention provides a new material for the indicated field of use, which material is distinguished by its extremely high and, moreover, even controllable material strength and utilizes the per se known class of oligohydroxycarboxylic acid poly(meth)acrylates, but does not employ initiator systems based on organoboron compounds.

Accordingly, the present invention relates to high-strength materials which are degradable and resorbable in the human and animal organisms and to molded articles manufactured therefrom, such as implants, based on cured (meth)acrylic acid esters of polyfunctionally hydroxyl-terminated oligomers of lower hydroxycarboxylic acids (hereinbelow designated as polyfunctional (meth)acrylic acid esters). Here the term (meth)acrylic acid esters is understood to include the corresponding esters of both acrylic acid and methacrylic acid, while also mixtures of these two ethylenically unsaturated acid components may be present in the same molecule.

The teaching according to the present invention is characterized in that both the materials and the molded articles manufactured therefrom for implantation into the living organism have been three-dimensionally cross-linked by radiation-curing and/or any other, however boron-free, free radical-initiated polymerization of the polyfunctional (meth)acrylic acid esters and exhibit a tensile strength of at least 10 $N/mm^2$.

It is preferred that the molded plastics articles have a tensile strength of at least 15 $N/mm^2$ and especially have respective values of at least 30 $N/mm^2$. Typical materials or molded articles within the scope of the invention have tensile strength values within the range of from about 40 to 60 $N/mm^2$. Thus, the tensile strength values are clearly higher than the typical strength values of healthy human bones. A method suitable for the determination of the tensile strength values will be described hereinbelow.

In addition, in a further embodiment of acting according to the invention it is possible to provide materials and/or molded articles of the type described, which with respect to kind and amount are free from physiologically questionable reaction aids and/or other additives from the production of the materials (hereinbelow designated as active contaminant) so that physiologically undesirable side-effects in the course of the physiological processes of the degradation and resorption of these implants in the body will not have to be suspected. In this embodiment, the invention, more specifically, makes allowance for the mini-constituents and traces of substances present in the final product in comparably concentrations which are introduced into the living organism upon implantation of the plastics-made member. One important cornerstone to be featured in greater detail hereinbelow of the invention is constituted by the parameters concretely selected for the production of the new materials and/or molded articles. Here, more particularly, t he invention provides an adjustment between the inhibitors of the polyfunctional (meth)acrylic acid esters, on the one hand, and the conditions for initiating the reaction of cross-linking these polyfunctional (meth)acrylic acid esters, on the other hand. This adjustment, effected in response to the kinds and amounts of the reactant auxiliary materials, results in that the auxiliary materials used in the production process, which materials inevitably remain incorporated in the solid material upon completion of the reaction, may be released and resorbed by the body without giving rise to doubts.

DETAILS OF THE TEACHING ACCORDING TO THE INVENTION

The teaching of the invention, in its nub, is directed to developing reactive components of the kind described and and therefrom forming materials and/or molded parts which now have been optimized with respect to the auxiliary materials—as inherently necessary in the sequential production steps—to achieve the maximum compatibility with the body. Here, the following is applicable:

It is basic chemical knowledge that the concomitant use of inhibitors of free radical formation is necessary to safely exclude any undesirable premature reaction of the system during its preparation, transportation and storage. Here, numerous compounds and/or systems are known in practice. For example, hydrides such as lithiumaluminium hydride, calcium hydride or sodium borohydride are to be considered. Further examples known for this purpose are phenols, phenol derivatives, hydroquinone and hydroquinone derivatives or, more specifically, phenothiazine.

Such free radical-inhibitors are required not only for the safe storage of the system to the date of the application thereof; it is rather necessary to employ such initiators already in the preparation of the free radical-reactive compounds—for example the polyfunctional (meth)acrylic acid esters—. Thus, one may distinguish between the so-called "preparation inhibitors" and the "application inhibitors", where both of these types of inhibitors may be same or different with respect to the kind and amount thereof. In the former case, the application inhibitor in general is identical with the preparation inhibitor already used in the preparation. However, the high gelling tendency of polyfunctional (meth)acrylic acid esters of the kind concerned demand the use of strongly active preparation inhibitors during the preparation thereof, the concomitant use of which can be undesirable in the intended application and, thus, ultimately as a constituent of the molded piece to be implanted into the living body.

According to one essential element of the invention the materials and/or implants described now are free from inhibitors that are undesirable with respect to the kind and/or amount thereof and would have remained from the preparation, storage and/or processing of the polyfunctional (meth)acrylic acid esters.

A particularly important example for a suitable inhibitor within the scope of the invention is constituted by tocopherol compounds and, among these, particularly α-tocopherol and, hence vitamin E.

The use in detail of physiologically acceptable tocopherol compounds and especially of vitamin E as an application inhibitor, but optionally already as a preparation inhibitor too, in combination with polyfunctional (meth)acrylic acid compounds of the kind also concerned by the invention is the subject matter of Applicants' older application P 39 39 161.2 (D 8930), the disclosure of which older protective right is incorporated herein by reference.

In order to complete the disclosure of the invention, the contents of this older application is briefly reported as follows. Vitamin E may be employed as the sole application inhibitor for stabilizing the polyfunctional (meth)acrylic acid ester, for which purpose the use thereof is preferred in amounts of from about 200 to 10,000 ppm, and usually within the range of from about 300 to 4,000 ppm,—each based on the weight of the radical-reactive material mixture—. In an important embodiment vitamin E is provided not only as the application inhibitor. Here vitamin E is also used already as the preparation inhibitor in the synthesis of the compositions intended to finally contact the living body. In this manner the transfer of undesired inhibitor components into the implants and, thus, into the living organism is prevented in an important embodiment. This is especially important in connection with the production of the polyfunctional (meth)acrylic acid esters which are known to be incapable of being subjected to a purification by distillation.

However, according to another embodiment of the invention it is also possible to exchange inhibitors, as has been described, more particularly, in Applicants' older application P 39 39 162 (D 8929). According to the teaching of this older protective right, appropriate compounds of the phenol type comprising hydroxyl groups capable of undergoing salt formation are employed which compounds after the preparation of the reactive components are subsequently bound and removed from the reaction mixture by way of a reaction with solid basic components, more specifically with solid oxides and/or hydroxides of the alkaline earth metals. The preparation inhibitor removed in this manner is then replaced by vitamin E as application inhibitor.

(Meth)acrylic acid esters of polyfunctional alcohols long ago were recognized and described as a class of substances that are extremely susceptible to undergo gelling. In order to reduce the susceptibility to a premature initiation and progress of the reaction, the state of prior art provides the use of solvents such as to reduce, by the dilution effect, the danger of early gelling taking place. According to prior art, the comparably low-volatile solvents are then stripped off by distillation, wherein it is often attempted to remove even the last remainders of the solvent by an extended treatment under high vacuum. However, it has been found that as a general rule a really complete removal of the solvents is difficult, so that thereby an additional source is formed of an unnecessary exposure to stress of the living organism upon implantation of molded articles made of such reactive systems. A preferred embodiment of the invention is designed to reliably eliminate even such stress. Thus, no solvents, and even less any physiologically dubious solvents, are a priori used here in the procedure of making the materials or molded articles according to the invention. In this context reference is made to the printed publications DE-A1 38 43 854, 38 43 938, 38 43 930 and 38 43 843, all of which have originated from Applicants.

Polyfunctional reactive components for composing the materials and molded articles according to the invention are oligomer components like those described in Applicants' previous publications DE-A1 32 04 504 and 32 29 635. These are systems which contain, as the polyfunctional (meth) acrylic acid esters, compounds that are liquid to solid at room temperature and contain at least two (meth)acrylate moieties on oligoester chains formed of hydroxycarboxylic acid ester chains. Compounds comprising from 2 to 4 (meth)acrylate moieties on the oligomer segments may be particularly suitable. In those types of compounds which are especially important for the formation of the auxiliary materials according to the invention there are present 2 and/or 3 (meth)acrylate moieties on the oligomer molecule, where the α,ω-positions of the (meth)acrylate moieties may be preferred especially in the case of the disubstituted oligomer segments.

The oligomer segments exhibit the structural feature

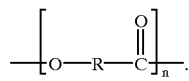

They are accessible by oligomerization of suitable hydroxycarboxylic acids or hydroxycarboxylic acid mixtures having the general formula

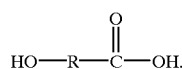

In a preferred embodiment of the invention, the groups —R— and n have been selected or adjusted to each other, respectively, so that the average molecular weight of the polyester oligomer unit is within the range of from about 100 to 600. Especially preferred values for the average molecular weight in this range are above 120, preferably at or above 150–200, and more particularly within the range of from about 300 to 500.

The polyester oligomer segment in a preferred embodiment is formed of monohydroxymonocarboxylic acids having up to about 10 carbon atoms in the molecule. Lower hydroxycarboxylic acids having from 2 to 6 carbon atoms are especially important. Hydroxycarboxylic acids especially suitable to form this central part of the polyfunctional (meth)acrylate compounds are glycolic acid, the various isomeric lactic acids, the optionally isomeric α- or β-hydroxypropionic acids, the optionally isomeric α-, β- or γ-hydroxybutyric acids and/or mixtures thereof. Definite isomers of said acids as well as any optional mixtures thereof may be employed. The most important representatives of the fundamental structures mentioned here are glycolic acids and lactic acid.

The polyester oligomers have been conveniently prepared by simultaneously using polyfunctional reactants. These co-reactants control the average molecular weight in the polyester oligomer. In addition, the selection of the functional groups of the co-reactants includes the chance of uniformly providing terminal hydroxyl groups or terminal carboxylic groups on the polyester oligomers.

The use of polyfunctional alcohols as co-reactants is preferred. Especially suitable are di- to tetrahydric alcohols. Here lower polyfunctional alcohols may be of special importance, with particular emphasis being laid on ethyleneglycol, the propanediols—and of these especially 1,2-propanediol—and glycerol.

The resulting products in all cases are modified oligoesters which in a per se known manner may be reacted to form the polyfunctional (meth)acrylic acid esters. If terminal hydroxyl groups are present on the oligoester, then the (meth)acrylic acid groups are introduced by esterification or transesterification with acrylic acid or acrylic acid esters and/or especially with the corresponding methacrylic acid compounds. However, the formation of suitable polyfunctional (meth)acrylic acid esters is also successfully accomplished upon the concomitant use of polyfunctional carboxylic acids as reactive co-reactants with primary formation of oligoesters with terminal carboxyl groups. Here the carboxyl-terminated oligomers as initially formed are reacted with polyhydric alcohols or derivatives thereof—for example with glycidyl esters of acrylic and/or methacrylic acids—. In this manner finally even here the type as required according to the invention of the polyfunctional (meth)acrylic acid ester oligomers may be produced, as has been described, for example, in DE-A1 32 29 635.

For attaining the objective according to the invention, i.e. to be enabled to produce the high-strength materials or implants shaped in a definite three-dimensional configuration with a reliable control of the active contaminants, in a preferred embodiment the physical condition of the polyfunctional (meth)acrylic acid esters at room temperature or moderately elevated temperatures is important. Here the invention prefers to process fluid or at least still pastous spreadable reactive materials, so that a shaping procedure intended to be carried out in advance to curing is facilitated or only made possible at all without using a solvent. This physical nature of the still uncured reactive material may also be important in connection with an incorporation in the molded bodies of fillers and/or for a layered configuration of said molded bodies, which aspect will be discussed hereinbelow. It may be preferred that the polyfunctional (meth)acrylate compounds possess a viscosity within the range of about from 500 to 70,000 mPa·s, preferably within the range of about from 3,000 to 50,000 mPa·s. The use of mixtures comprising a plurality of such oligomer-based reactive components of different compositions and, hence, different physical properties is included in the teaching according to the invention. It is just in this context that an embodiment may be of importance which contemplates the concomitant use of so-called reactive diluents which, more specifically, are to be attributed to the class of monofunctional (meth) acrylic acid esters. Co-reactants of this kind are integrated in the polymer structure during the three-dimensional cross-linking process to form the high-strength materials and shaped articles.

A sufficient Theological behavior of the polyfunctional (meth)acrylic acid esters at room temperature or moderately elevated temperatures—for example up to about 50° C. to 60° C.—may also be essential with view to the following considerations. The essential process step in the production of the novel three-dimensionally cross-linked materials and shaped articles is curing the composition by a specific reaction of the ethylenically unsaturated (meth)acrylic acid moieties on the oligomer molecule proceeding with the simultaneous formation of three-dimensional cross-linkages. The initiation of this reaction may be effected in various ways. Within the objective of the invention, the governing principle also here must be to restrict the reaction aids to be possibly included in this connection (initiators, starter systems and the like) with respect to kinds and amounts thereof in a manner so that the residual substances released therefrom upon the degradation thereof do not cause any physiological problems. More specifically, one important feature thereof is that it is possible to homogeneously incorporate the auxiliary materials, if concomitantly used, in the reactant(s) to be cured. It is the rheology preferred according to the invention of the uncured material that favors, or only makes possible at all, the formation of such homogeneous mixture.

Two per se known mechanisms of reaction are more specifically contemplated here for the initiation of the curing reaction proceeding via free-radicals, viz. radiation-induced curing and the use free radical-initiator systems.

The reactive systems of the type according to the invention are susceptible to radiation curing even at lower working temperatures. More specifically, they are suitable to undergo an intiation of the reaction also in the absence of photoinitiators. Thus, upon photopolymerization, especially upon the exposure to UV light, molded articles can be manufactured that have been photocured in situ and, due to the polyfunctional monomer character, have a molecular weight of virtually infinity and exhibit very high strength values.

By way of the simple photoinitiated polymerization there may be readily produced molded articles of any optional shape. In the course thereof, UV light curing may be carried out stepwise in a manner so that the material is pre-cured and shape-stabilized in a first step, while in a subsequent irradiation step full curing of the material is accomplished. It may be ensured by cooling—for example by cooling with water—that predetermined peak temperatures in the shaped body will not be exceeded. In this case it may be necessary to exclude any direct contact with the cooling water of the shaped body being cured.

Other types of reaction-inducing radiation may be employed, e.g. a laser beam, X-ray radiation or gamma radiation. The concomitant use of per se known initiators is possible; in this context reference is made, for example, to the printed instructions in Enzyl. Polym. Sci. and Eng. (2nd Edition) Vol. 11, 187–207, and pertinent commercial products, for example from the companies Merck, Darmstadt (DE), and Ciba-Geigy, Switzerland.

However, according to the invention it is also possible to cure the shaped reactive material by free radical-initiated chemical polymeriation in a per se known manner. The selection of known reaction aids to be used here is facilitated by the following: In the state of the art there is known a variety of redox systems based on peroxidic compounds that are used in combination with reducing agents and/or metal compounds of such metals that can occur in several valence states.

In this context, for example, reference is made to the comprehensive review in Progress in Polymer Science, Vol. 8, Pergamon Press, Oxford-New York, 1982, pages 61–131 and the voluminous primary literature referred to therein.

If suitable redox systems are to be selected, which do not give rise to substantial physiological doubts, especially with view to kind and amount of residual matter remaining in the cured material, the following complex of facts speaks in favor of acting within the scope of the invention: According to prior art, reactant systems that in comparison to others are physiologically more acceptable have been described especially in the context of aqueous polymerization systems. The material to be cross-linked according to the invention is a per se non-aqueous (anhydrous) system. Nevertheless, said material, due to its oligomer structure derived from lower hydroxycarboxylic acids, in many cases is capable of also dissolving such components as otherwise employed in the aqueous systems. Thereby it becomes possible to achieve a really homogeneous distributon of physiologically largely acceptable activator systems also in the anhydrous reaction phase of the polyfunctional (meth)acrylic acid esters, thereby to effect cross-linking to take place at the predetermined temperatures.

Here the following substances may be mentioned just as examples from the large class of components suitable as such redox systems: Peroxide compounds such as peracids, diacyl peroxides, hydroperoxides and the like, among which compounds physiologically acceptable acids, for example the so-called edible acids, may be of particular importance of the peroxide-forming component. From the large class of activators and/or reducing agents, compounds such as ascorbic acid, sorbose, fructose, dextrose and other sugars, offer themselves, virtually all of which are physiologically acceptable components.

Metal compounds suitable for stimulating and activating the redox reaction are derived, in a particular case, from iron which in the form 2- and/or 3-valent iron may be added to the redox systems in a per se known manner. For example, admixing the iron to form a homogeneous mixture is especially safely achieved with the corresponding salts of glycolic acid and/or of lactic acid. The invention allows to make high-strength materials and molded articles within the definition as initially given of the minimum values of the primary tensile strength. Applicable to the determination of these values are the Standard Conditions as in detail set forth in the introduction to the Examples' section.

In a special embodiment of the invention, the novel materials and/or molded articles are characterized by a content of filler. These fillers are preferably present in a discrete solids phase and may be both inorganic as well as organic in nature. The preferred representatives of these classes of fillers are themselves resorbable in the body or at least acceptable to the body. Examples of inorganic fillers of this kind are body-compatible ceramic materials, especially so-called bioactive ceramic materials in powderized and/or granular forms. Known examples thereof are tricalcium phosphate and/or hydroxylapatite in the unsintered or sintered state. In this context reference is made, for example, to the DE-Al 38 25 211 and 38 26 915, wherein improved, predominantly body-resorbable bone waxes and new materials for bone substitutes and for combining bone and/or prosthesis materials, respectively, have been described.

Another class comprises fillers having a fibrous structure. Due to the reinforcement with fibrous fillers and/or fiber-made filler materials the required material properties may be additionally positively affected.

Thus, in a first embodiment, materials and/or molded articles of the kind according to the invention have been additionally reinforced with staple fibers. In one possible embodiment, the staple fibers are incorporated in the still fluid uncured polyfunctional (meth)acrylic acid ester material and then firmly integrated by the subsequent curing step. In an especially interesting embodiment the incorporation in the molded article or material of fiber bundles, and more particularly of appropriate materials having filament structure, is provided. Thus, it is possible, for example, to form pin-like materials centrally around such filaments or bundles of filaments. Here it may be intended to integrate the filler fibers and/or filament materials in a pre-stretched condition in the three-dimensional network so that the high-tenacity properties of such pre-stretched filaments are directly imparted to the molded article within the scope of the invention.

In other embodiments of the invention, in addition to or in the place of the fiber reinforcement described above, filament-based materials such as nets, woven fabrics, knitted fabrics and the like are incorporated in the material to be cured and in this condition are integrated in the three-dimensional network. Thus, more specifically, an envelope of a material rod within the scope of the invention may be provided with an appropriate fiber sheet in its outer regions, or an appropriate fiber sheet material is helically wound thereon, thoroughly impregnated with the fluid polyfunctional (meth)acrylic acid ester material and cured to form a high-strength molded article. As has already been set forth, the fillers and, thus, especially also the fibers indicated here have preferably been formed of a body-resorbable material. In this respect there offer themselves, more particularly, fibers or filaments or consecutive materials recovered therefrom based on high polymers of glycolic acid and/or lactic acid. A high-tenacity filamentous poly(lactic acid) material is known and widely accepted as suture material in the surgical technique. Suitable, however, are also polypeptide-based filaments. A pretreatment of the fiber surface may be expedient in order to increase the adhesion bond.

In addition to or also in the absence of such additional materials another modification of the novel high-strength materials and/or shaped articles may be provided according to the invention. This comprises the following elements: A certain shaped body may be made not only of one defined uniform three-dimensional cross-linkable oligomer material—be it in the form of a definitely selected polyfunctional (meth)acrylic acid ester or a preferably homogeneous mixture of several esters of this kind—, but what is also possible is to provide a preferably layered structure of the molded bodies of appropriate materials different in nature. Thus, shaped articles having such a layered structure may comprise, for example, layers of materials which are resorbed comparably faster and at least one layer of material having a reduced hydrophilicity and/or an increased stability to hydrolysis. Here it may be preferred to locate the material layer(s) which are resorbed comparably faster in the inner region of the shaped article and to cover the resulting core with one or more layer(s) of higher hydrolysis-resistant matter. Such core consisting of one or material layer(s) having an increased degradation rate may be covered against the outside at least portionwise by one or more material layer(s) having a higher resistance to penetration by the aqueous body liquid.

The peculiarity of such an embodiment of the shaped article is immediately evident: Upon implantation of the shaped article, for example as a pin, into a fractured tubular bone there is first required a sufficient function of the pin under stress for an extended period of time. This requirement persists at least as long as it takes until the fracture will have regained its own strength due to regenerative bone growth. Once this latter condition will have been reached, a comparably faster degradation of the implanted pin material can be tolerated or even be desired. The option as outlined here of providing such implants having a layered structure allows the properties altogether of the implant to be optimally adapted not only to the needs immediately after transplantation but also to the needs within the further course of the healing and resorption process.

The potential susceptibility to hydrolysis of the three-dimensionally cross-linked materials, e.g. of the shaped articles, and the decrease associated therewith in the strength properties may make it altogether desirable, to provide one or more layer(s) of materials exhibiting an increased resistance to penetration by moisture especially in the outer region. Nevertheless, in the preferred embodiment even these layers are to be ultimately degradable. Here it has been found that again especially the lactic acid-based polymer materials having a reduced hydrophilicity can be suitable auxiliary materials within the scope of the invention. Thus, for example a three-dimensional material piece within the scope of the invention may be immersed in molten poly(lactic acid), whereby cover layers of poly(lactic acid) having a pre-determined thickness may be coated thereon. If desired, a three-dimensional (meth)acrylic acid ester material within the scope of the invention may be applied onto such a cover layer. Hereby an undesirable lesion of the cover layer having an increased water-resistance can be safely prevented in the implantation. Also suitable are cover layers or intermediate layers based on the hydroxycarboxylic acids next in the number of carbon atoms, more specifically poly(hydroxybutyrate) or poly(hydroxybutyrate-co-hydroxyvalerate).

Eventually, the invention may utilize the fact that the stability to hydrolysis of the cross-linked (meth)acrylic acid ester material may be affected by suitably selecting the constituents to form the oligomeric molecular cores. Lactic acid derivatives are known to be significantly more resistant to hydrolysis than comparable derivatives of glycolic acids. In the same manner, for example, 1,2-propanediol is more oleophilic than the methyl group-free ethyleneglycol. Accordingly, as has been suggested above, the invention provides, for example, a design wherein the core of the shaped article is composed of a comparably fast-degradable material based on oligoglycolic acid/ethyleneglycol, whereas the demanded use-life of the desired strength values is accomplished by that the outer regions of the material piece are made of product(s) derived from lactic acid oligoester(s), with the concomitant use, if so desired, of polyhydric alcohols exhibiting a higher oleophilicity to control the molecular weight.

The invention, in a particular embodiment, also pertains to the case where active medical ingredients are included at least portionwise in the shaped article, especially in the cross section of the shaped article. Here, use is made of the per se known depot effect provided by oligomers of lactic acid and/or glycolic acid for the incorporation and time-controlled release of such active medical ingredients. Examples of such active medical ingredients include disinfectant and/or antibacterial agents, especially antibiotics and even more specifically wide-spectrum antibiotics. Other examples such active medical ingredients include antiallergenic agents and/or agents for stimulating the tissue and/or bone growth. These classes of compounds here listed just by way of example may be almost ad libitum extended, depending on the particular requirements.

The implants may have any optional shape in space. Suitable three-dimensional shapes include, for example, rods, plates, splints, pins, screws, gridlike elements and the like. The invention includes the series production of suitable standardized materials for surgical practice as well as the individual manufacture of work pieces adapted to suit the need of an individual case, and especially the manufacture in situ of the respective shaped articles.

EXAMPLES

The values of the physical strength, and especially of tensile strength, elongation at break and modulus of elasticity, are determined using test specimens which are prepared according to the following procedure:

The feedstock based on the reactive polyfunctional (meth) acrylic acid ester is cast by means of an aluminum mold to give a spatula-like solid body of pre-defined dimensions ("test bone") and is cured in this mold.

The details are as follows:

The test bone is shaped as a rod-like body having a rectangular cross section, the narrow middle part of which widens towards both ends of the shaped body.

| Dimensions of the test bone: | |
|---|---|
| Total length: | 74 mm |
| Thickness: | 1.9 mm |
| Length of the narrow middle part: | 27 mm |
| Width of the narrow middle part: | 4 mm |
| Width of the two terminal portions: | 12 mm. |

The aluminum mold consists of two parts connectable by screws, so that it is made easier to remove the cured test bone from the mold. When the composition to be cured is cast into the mold, the following is to be observed:

The monomer must be bubble-free. When the mix is poured into the mold, no bubbles must be formed at the edges (especially along the narrow part of the bone). Thus, it is recommended first to cover the edges of the mold using a syringe with a needle, and only thereafter to completely fill up the mold. Then the exposed surface is stripped off using a slide in order to obtain a smooth surface.

Curing:

The following light source is employed for curing: UV ASpot 400/T, 400 W, 200/230 V; Dr. Hönle GmbH.

The UV bulb has a wattage of 400 W; the distance from the illuminated object is 22 cm. The intensity of the UV radiatior is determinative, among other factors, of the curing time.

The following UV A radiation output powers were determined:

| 1. In the middle of the chamber: | 31.2 mW/cm$^2$ |
| --- | --- |
| 2: At the border of the chamber: | about 25.1 mW/cm$^2$. |

Strength values:

The cured bones were torn on a tension tester of the company Zwick at a tear speed of 5 mm/min. The tensile strength is measured as a function of the curing time:

Tensile tests with test bones made of cured oligo(glycolic acid-ethyleneglycol, 4:1)bis-methacrylate

| Sample length: | 27 mm |
| --- | --- |
| Sample width: | 4 mm |
| Sample thickness: | 1.9 mm |

| | Curing | -(each average of three experiments)- | | |
| --- | --- | --- | --- | --- |
| Example No. | Time UV 400 W hours | Tensile strength N/mm$^2$ | Elongation at break % | Modulus of elasticity N/mm$^2$ |
| 1 | 3 | 59.1 | 14.9 | 430 |
| 2 | 8 | 84.8 | 18.7 | 568 |
| 3 | 12 | 77.7 | 16.1 | 572 |

It is seen that there is a maximum of the tensile strength at about 8 hours of curing time. The modulus of elasticity also reaches its maximum after this time.

UV-curing of the monomer admixed with photoinitiator:

In order to shorten the curing time, the monomer was admixed with two different photoinitiators and then cured. The following photoinitiators were used:

1. Irgacure 651/company Merck:

A solution of 1% by weight dissolved in the monomer.

2. 4-(2-Acryloyloxyethoxy)phenyl-(2-hydroxy-2-propyl) ketone/company Merck:

Solutions of 1% by weight or of 3% by weight, respectively, dissolved in the monomer.

Tensile tests with test bones made of cured oligo(glycolic acid-ethyleneglycol, 4:1)bis-methacrylate with the photoinitiator Irgacure 651

| Example No. | Initiator concentration % | Curing Time UV 400 W hours | Tensile shear strength N/mm$^2$ | Modulus of elasticity N/mm$^2$ |
| --- | --- | --- | --- | --- |
| | | | - (each average of three experiments) - | |
| 4 | 1 | 2 | 36.2 | 301 |
| 5 | 1 | 4 | 40.9 | 340 |

Tensile tests with test bones made of cured oligo(glycolic acid-ethyleneglycol, 4:1)bis-methacrylate with the photoinitiator 4-(2-Acryloyloxyethoxy)phenyl-(2-hydroxy-2-propyl)ketone

| Example No. | Initiator concentration | Curing Time UV 400 W hours | Tensile shear strength N/mm$^2$ | Modulus of elasticity N/mm$^2$ |
| --- | --- | --- | --- | --- |
| | | | - (each average of three experiments) - | |
| 6 | 1 | 4 | 43.7 | 312 |
| 7 | 1 | 8 | 60.8 | 329 |
| 8 | 3 | 4 | 72.8 | 479 |

Fiber reinforcement In the same manner as described above, 10% by weight of short fibers of about 4 mm in length, cut from Polyglactin 910 fibers (Sutupak) of the company Ethicon/2000, Norderstedt, were embedded in the monomer, and the mixture was cured. The results were as follows:

| Example No. | Curing Time hours | Number of fibers | Tensile strength N/mm$^2$ | Elongation at break % |
| --- | --- | --- | --- | --- |
| 9 | 3 | random laid nonwoven fabric | 44.08 | 14.7 |
| 10 | 6 | random laid nonwoven fabric | 45.35 | 12.1 |

As the polyfunctional (meth)acrylate compound there is employed the oligoglycolic acid (Pn=4) bismethacrylate as already described in the older patent application P 39 39 161.2, the preparation of which is once more described hereinbelow:

Preparation of the oligoglycolic acid bismethacrylate:

A vitamin E-stabilized reactive component based on oligoglycolic acid/bis-methacrylate is prepared in the following process steps:

First, an oligomer having terminal hydroxy groups is prepared from glycolic acid and ethylene glycol in a molar ratio of 4:1. Then, commercially available methacrylic acid with the addition of phenothiazine as stabilizer component is freed from its inhibitor content by distillation under a water-jet vacuum. The methacrylic acid collected as distillate is stabilized with vitamin E. Then the oligo-glycolic acid pre-condensate is esterified with the methacrylic acid in the solvent-free system in the presence of p-toluenesulfonic acid as catalyst and upon addition of a further amount of vitamin E. The progress of the esterification reaction is monitored. If required, small additional metered amounts of methacrylic acid will be subsequently added.

The resulting reaction product is eventually rendered acid-free by way of a dry neutralization with calcium hydroxide, and thereafter the solid neutralizing agent is removed therefrom over a pressurized filter.

The process steps as carried out are in detail described hereinbelow; the process is operated in a plurality of batches. The ageing behavior of the oligoglycolic acid pre-condensates stored in the absence of air is determined over the period of one year. It was be observed that the product properties remained constant.

In detail, the following is applicable:

1.1 Preparation of the glycolic acid/ethylene glycol 4:1 oligomer

A 25 l test reactor was charged with 16.72 kg of glycolic acid and 3.41 kg of ethylene glycol. The crystal pulp was melted in an inert atmosphere under a nitrogen stream and then further heated to a maximum temperature of 145° C. to 150° C. (bottoms temperature). After the reaction had started with distillation of water, it was continued for 11 hours until no more reaction water was formed (drop in the vapor temperature to 70° C. to 73° C. at a conversion of 70%). The aqueous solution obtained upon distillation was analyzed for the quantity of distillate, the acid value (glycolic acid contents) and the water contents by the Karl Fischer method. In order to lead the reaction to completion, the mixture was carefully evacuated to 400 Torr, and the pressure was further reduced to 10 Torr within 2 hours and maintained at this level for 1 hour, in order to remove the residual water of reaction for accomplishing a quantitative conversion.

The additional amount of condensate was collected for quantification in a cold trap (cooled with dry ice and ethanol). After the total period of reaction, the mixture was cooled to 100° C. and re-pressurized to atmospheric pressure with nitrogen, and the product was dispensed while still hot. The product was directly used for the preparation of oligo-glycolic acid bis-methacrylate without further purification. Yield: 97.7%.

Analytical results of the oligomer

| Designation | Immediately after the preparation | 1 Month old | 1 Year old |
| --- | --- | --- | --- |
| Batch size kg | 20 | 4.5 | 2 |
| Consistency | pastous | pastous | pastous |
| Viscosity at room temperature mPa · s (Epprecht Viscosimeter MK4) | 12,500 | 13,000 | 12,800 |
| Molecular weight | | | |
| $M_n$* | 438 | 455 | 454 |
| $M_w$ | 515 | 533 | 530 |
| Free glycolic acid % | 2.1/2.2 | 1.4 | 1.9 |
| Free ethylene glycol % | 0.2 | 0.2 | 0.2 |
| Saponification value | 765.4 | 754.4 | 754.0 |
| Behavior in water | | | |
| pH after 2 minutes | 3.8 | 3.8 | 3.8 |
| pH after 60 minutes | 3.4 | 3.4 | 3.4 |
| Peroxide content | negative | | |

*Determination of the molecular weight as GPC analysis. Since the calibration was effected with polyethylene glycol as standard, the difference between $M_n$ in theory and $M_n$ as found is due to the calibration method.

1.2 Oligo-glycolic acid bis-methacrylate

Commercially available methacrylic acid (company Roehm) is newly inhibited with vitamin E according to the following procedure:

In a vacuum distillation apparatus, 15 moles (=1,291.35 g) of methacrylic acid (b.p. 163° C.) are admixed with 3.87 g (=3,000 ppm) of phenothiazine (as stabilizer); the methacrylic acid was distilled off under a strong stream of air in a water-jet vacuum. 100 ppm of vitamin E (Covitol F-1000-2, 67%, Henkel KGaA) (=139 mg/l) are placed in the receiver, and the methacrylic acid is distilled with stirring. The distillation is stopped, once 932 g of the methacrylic acid have been collected after distillation.

1.3 Course of the reaction

A three-neck flask equipped with stirrer, Claisen head and condenser ("distillation bridge") was charged with 294 g of oligo-glycolic acid, 206.4 g methacrylic acid and 17.5 g of p-toluenesulfonic acid; the mixture was inhibited with 0.86 g of vitamin E (a-tocopherol). Throughout the reaction, air was passed through the mixture at a rate of at least 40 l/h.

The esterification was effected at a maximum temperature of 105° C. by removal of the water formed, until the quantity of water removed was more than 35.78 g (more than 97% conversion).

The distillation receiver was cooled with a dry ice/ethanol mixture throughout the reaction. At a maximum bottoms temperature of 105° C. and a pressure of 500 mbar the esterification time was between 12 and 14.5 hours at a total conversion of from 97 to 98.5%. The aqueous solution (as recovered from the receiver and cold trap) was sampled every 1.5 hours and was analyzed for the quantity of distillate, the acid value (methacrylic acid contents) and the water contents by the Karl Fischer method.

The water content and the amount of methacrylic acid as entrained in the distillation were calculated from the differences; after each determination, it was checked whether enough methacrylic acid was still available for the reaction. In most cases, additional 0.1 moles of methacrylic acid had to be replenished after about 7.5 or 8 hours.

Upon completion of the reaction (conversion in excess of 97%) the product was dispensed for purification.

1.4 Work-up of the reaction product

In the end of the reaction period, the product is not quite free from acid. Therefore, it was neutralized with $Ca(OH)_2$. Since in the determination of the acid value, due to the water required for the determination, the product underwent hydrolysis and a continuously increasing amount of acid was released by this reaction, it was not possible to determine the acid content by titration.

Therefore, the acid value had to be theoretically calculated.

The amount of $Ca(OH)_2$ calculated to be required for neutralization was introduced into the warm reaction product and allowed to react at 105° C. and 500 mbar with stirring and 40 l/h of air being passed through the mixture for 30 minutes.

The neutralized product (highly viscous at 100° C. to 105° C.) is filtered by means of a pressurized nutsch filter and a Loeffler filter (80 NM012) at 100° C. to 105° C. under 3 bar. Then, the product—while still hot—was once more filtered under otherwise the same conditions through a round filter (NNG 16, medium filtering speed).

What is claimed is:

1. A composition of matter useful as a high-strength material which is degradable and resorbable in the human and animal organisms comprising cured (meth)acrylic acid esters of polyfunctionally hydroxyl-terminated oligomers of lower hydroxycarboxylic acids, wherein said (meth)acrylic acid esters of polyfunctionally hydroxyl-terminated oligomers of lower hydroxycarboxylic acids have been prepared under solvent-free conditions in the steps of the production of the oligomer(s), the conversion thereof to the polyfunctional (meth)acrylic acid esters and the curing-shaving thereof, and three-dimensionally cross-linked by boron-free, free radical-initiated polymerization and exhibit a tensile strength of at least 10 $N/mm^2$.

2. A composition of claim 1 wherein said cured (meth) acrylic acid esters of polyfunctionally hydroxyl-terminated oligomers of lower hydroxycarboxylic acids have a tensile strength of at least 15 $N/mm^2$.

3. A composition of claim 1 wherein said cured (meth) acrylic acid esters of polyfunctionally hydroxyl-terminated oligomers of lower hydroxycarboxylic acids have a tensile strength of at least 30 to 40 $N/mm^2$.

4. A composition of claim 1 wherein said composition is substantially free from reaction aids, solvents and other additives added in the production process, which aids, solvents and additives, with respect to kinds and/or amounts, are physiologically undesirable.

5. A composition of claim 1 wherein any inhibitors to the polyfunctional (meth)acrylic acid esters from which said composition is cured, and the initiators of the step of cross-linking, have been selected so that any residues thereof left in the materials and implants are physiologically acceptable with respect to kinds and/or amounts thereof.

6. A composition of claim 1 further comprising vitamin E as a result of the use thereof as a reaction inhibitor.

7. A composition of claim 1 wherein said composition has been cured by radiation to exhibit the required primary tensile strength.

8. A composition of claim 1 wherein said composition by UV radiation in the absence of an initiator.

9. A composition of claim 1 wherein said cured (meth)acrylic acid esters of polyfunctionally hydroxyl-terminated oligomers of lower hydroxycarboxylic acids are derived from appropriate compounds of hydroxycarboxylic acids comprising up to 10 carbon atoms.

10. A composition of claim 1 wherein said cured (meth)acrylic acid esters of polyfunctionally hydroxyl-terminated oligomers of lower hydroxycarboxylic acids comprise from 2 to 6 carbon atoms.

11. A composition of claim 1 wherein said cured (meth)acrylic acid esters of polyfunctionally hydroxyl-terminated oligomers of lower hydroxycarboxylic acids are selected from the group consisting of glycolic acid, lactic acid, hydroxypropionic acid and/or hydroxybutyric acid.

12. A composition of claim 1 wherein said cured (meth)acrylic acid esters of polyfunctionally hydroxyl-terminated oligomers of lower hydroxycarboxylic acids are derived from hydroxycarboxylic acids polyfunctionally terminated with hydroxyl groups by the concomitant use of either (i) polyhydric alcohols or (ii) polybasic carboxylic acids followed by a reaction with polyhydric alcohols and/or derivatives thereof.

13. A composition of claim 1 wherein said cured (meth)acrylic acid esters of polyfunctionally hydroxyl-terminated oligomers of lower hydroxycarboxylic acids are derived from polyfunctional (meth)acrylic acid esters having from 2 to 4 (meth)acrylic acid moieties in the molecule.

14. A composition of claim 1 wherein said cured (meth)acrylic acid esters of polyfunctionally hydroxyl-terminated oligomers of lower hydroxycarboxylic acids are derived from polyfunctional (meth)acrylic acid esters having from 2 (meth)acrylic acid moieties in the molecule.

15. A composition of claim 1 wherein said cured (meth)acrylic acid esters of polyfunctionally hydroxyl-terminated oligomers of lower hydroxycarboxylic acids are derived from oligomers of glycolic acid and/or of lactic acid prepared with the concomitant use of ethyleneglycol, 1,2-propanediol, 1,3-propanediol and/or glycerol to provide the polyfunctional termination with hydroxyl groups with simultaneous control of the average molecular weight.

16. A composition of claim 1 wherein said cured (meth)acrylic acid esters of polyfunctionally hydroxyl-terminated oligomers of lower hydroxycarboxylic acids are derived from hydroxyl-terminated hydroxycarboxylic acid oligomer having an average molecular weight of about from 100 to 600.

17. A composition of claim 1 wherein said cured (meth)acrylic acid esters of polyfunctionally hydroxyl-terminated oligomers of lower hydroxycarboxylic acids are derived from hydroxyl-terminated hydroxycarboxylic acid oligomer having an average molecular weight of about from 200 to 500.

18. A composition of claim 1 further comprising fillers in a discrete solids phase, said fillers being also resorbable by the body.

19. A composition of claim 1 further comprising fillers having a fibrous structure in the form of staple fibers.

20. A composition of claim 1 further comprising fillers having a filament structure.

21. A composition of claim 20 wherein said fillers are selected from the group consisting of nets, woven fabrics, and knitted fabrics.

22. A composition of claim 20 wherein said filament structure is in a prestretched condition incorporated by curing in the three-dimensional network.

23. A composition of claim 1 further comprising fillers comprised of fibers based on glycolic acid and/or lactic acid.

24. A composition of claim 1 further comprising fillers comprised of fibers based on poly(lactic acid) or polypeptide.

25. An article of manufacture useful as a high-strength surgical implant which is degradable and resorbable in the human and animal organisms comprising a shaped form of cured (meth)acrylic acid esters of polyfunctionally hydroxyl-terminated oligomers of lower hydroxycarboxylic acids, wherein said (meth)acrylic acid esters of polyfunctionally hydroxyl-terminated oligomers of lower hydroxycarboxylic acids have been three-dimensionally cross-linked by boron-free, free radical-initiated polymerization and exhibit a tensile strength of at least 10 $N/mm^2$.

26. An article of claim 25 wherein said article has a layered structure wherein layers of materials which are resorbed comparably faster have been covered with at least one layer of a material having a reduced hydrophilicity or an increased stability to hydrolysis.

27. An article of claim 26 wherein said article has as a core or towards the core thereof, one or more material layers having an increased degradation rate which layers have been covered against the outside at least portionwise by one or more material layers having a higher resistance to penetration by the aqueous body liquid of the environment of use of such article.

28. An article of claim 26 comprising polymer substances based on lactic acid and or 1,4-hydroxybutyric acid forming material layers having an increased water-resistance.

29. An article of claim 25 further comprising active medical ingredients, at least portionwise in the shaped article.

30. An article of claim 25 further comprising active medical ingredients in the cross section of said article.

31. An article of claim 30 wherein said active medical ingredients are selected from the group consisting of agents having disinfectant or antibacterial effects, antiallergenic agents, agents for stimulating the tissue or bone growth.

32. An article of claim 30 wherein said active medical ingredient is a wide-spectrum antibiotic.

33. An article of claim 25 wherein said article is shaped as a member selected from the group consisting of rods, plates, splints, pins, and screws.

34. An article of claim 25 wherein said cured (meth)acrylic acid esters of polyfunctionally hydroxyl-terminated oligomers of lower hydroxycarboxylic acids have a tensile strength of at least 15 $N/mm^2$.

35. An article of claim 25 wherein said cured (meth)acrylic acid esters of polyfunctionally hydroxyl-terminated oligomers of lower hydroxycarboxylic acids of at least 30 to 40 $N/mm^2$.

36. An article of claim 25 wherein said article is substantially free from reaction aids, solvents and other additives added in the production process, which aids, solvents and additives, with respect to kinds and/or amounts, are physiologically undesirable.

37. An article of claim 25 wherein any inhibitors to the polyfunctional (meth)acrylic acid esters from which said article is formed, and the initiators of the step of cross-linking, have been selected so that any residues thereof left in the article are physiologically acceptable with respect to kinds and/or amounts thereof.

38. An article of claim 25 further comprising vitamin E as a result of the use thereof as a reaction inhibitor.

39. An article of claim 25 wherein said cured (meth) acrylic acid esters of polyfunctionally hydroxyl-terminated oligomers of lower hydroxycarboxylic acids have been prepared under solvent-free conditions in the steps of the production of the oligomer(s), the conversion thereof to the polyfunctional (meth)acrylic acid esters and the curing-shaping thereof.

40. An article of claim 25 wherein said cured (meth) acrylic acid esters of polyfunctionally hydroxyl-terminated oligomers of lower hydroxycarboxylic acids have been cured by radiation to exhibit the required primary tensile strength.

41. An article of claim 25 wherein said cured (meth) acrylic acid esters of polyfunctionally hydroxyl-terminated oligomers of lower hydroxycarboxylic acids have been cured by UV radiation in the absence of an initiator.

42. An article of claim 25 wherein said cured (meth) acrylic acid esters of polyfunctionally hydroxyl-terminated oligomers of lower hydroxycarboxylic acids are derived from appropriate compounds of hydroxycarboxylic acids comprising up to 10 carbon atoms.

43. An article of claim 25 wherein said cured (meth) acrylic acid esters of polyfunctionally hydroxyl-terminated oligomers of lower hydroxycarboxylic acids comprising from 2 to 6 carbon atoms.

44. An article of claim 25 wherein said cured (meth) acrylic acid esters of polyfunctionally hydroxyl-terminated oligomers of lower hydroxycarboxylic acids selected from the group consisting of glycolic acid, lactic acid, hydroxypropionic acid and/or hydroxybutyric acid.

45. An article of claim 25 wherein said cured (meth) acrylic acid esters of polyfunctionally hydroxyl-terminated oligomers of lower hydroxycarboxylic acids are derived from hydroxycarboxylic acids polyfunctionally terminated with hydroxyl groups by the concomitant use of either (i) polyhydric alcohols or (ii) polybasic carboxylic acids followed by a reaction with polyhydric alcohols and/or derivatives thereof.

46. An article of claim 25 wherein said cured (meth) acrylic acid esters of polyfunctionally hydroxyl-terminated oligomers of lower hydroxycarboxylic acids are derived from polyfunctional (meth)acrylic acid esters having from 2 to 4 (meth)acrylic acid moieties in the molecule.

47. An article of claim 25 wherein said cured (meth) acrylic acid esters of polyfunctionally hydroxyl-terminated oligomers of lower hydroxycarboxylic acids are derived from polyfunctional (meth)acrylic acid esters having from 2 (meth)acrylic acid moieties in the molecule.

48. An article of claim 25 wherein said cured (meth) acrylic acid esters of polyfunctionally hydroxyl-terminated oligomers of lower hydroxycarboxylic acids are derived from oligomers of glycolic acid and/or of lactic acid prepared with the concomitant use of ethyleneglycol, 1,2-propanediol, 1,3-propanediol and/or glycerol to provide the polyfunctional termination with hydroxyl groups with simultaneous control of the average molecular weight.

49. An article of claim 25 wherein said cured (meth) acrylic acid esters of polyfunctionally hydroxyl-terminated oligomers of lower hydroxycarboxylic acids are derived from hydroxyl-terminated hydroxycarboxylic acid oligomer having an average molecular weight of about from 100 to 600, and especially of about from 200 to 500.

50. An article of claim 25 wherein said cured (meth) acrylic acid esters of polyfunctionally hydroxyl-terminated oligomers of lower hydroxycarboxylic acids are derived from hydroxyl-terminated hydroxycarboxylic acid oligomer having an average molecular weight of about from 200 to 500.

51. An article of claim 25 further comprising fillers in a discrete solids phase, said fillers being also resorbable by the body.

52. An article of claim 25 further comprising fillers having a fibrous structure in the form of staple fibers.

53. An article of claim 25 further comprising fillers having a filament structure.

54. An article of claim 53 wherein said fillers are selected from the group of nets, woven fabrics, and knitted fabrics.

55. An article of claim 53 wherein said filament structure is in a pre-stretched condition incorporated by curing in the three-dimensional network.

56. An article of claim 25 further comprising fillers comprised of fibers based on glycolic acid and/or lactic acid.

57. An article of claim 25 further comprising fillers comprised of fibers based on poly(lactic acid) or polypeptide.

* * * * *